United States Patent [19]
Crawford

[11] Patent Number: 6,059,737
[45] Date of Patent: May 9, 2000

[54] ADHESIVE GASKET FOR BLOOD COLLECTION NEEDLES

[75] Inventor: Jamieson William Maclean Crawford, New York, N.Y.

[73] Assignee: Becton Dickinson and Company, Franklin Lakes, N.J.

[21] Appl. No.: 09/164,269

[22] Filed: Sep. 30, 1998

[51] Int. Cl.[7] .......................................................... A61B 5/00

[52] U.S. Cl. ............................................................ 600/576

[58] Field of Search ................................... 600/576, 577; 604/187, 192, 198, 263, 411–413, 415, 533, 538, 539

[56] References Cited

U.S. PATENT DOCUMENTS

| | | |
|---|---|---|
| 4,834,715 | 5/1989 | Hanifl . |
| 5,102,397 | 4/1992 | Brunet ..................................... 600/577 |
| 5,133,362 | 7/1992 | Moss ........................................ 600/576 |
| 5,586,977 | 12/1996 | Dorsey ..................................... 600/537 |
| 5,639,525 | 6/1997 | Kuhn et al. . |
| 5,782,820 | 7/1998 | Roland . |

*Primary Examiner*—Max Hindenburg
*Attorney, Agent, or Firm*—Nanette S. Thomas, Esq.

[57] ABSTRACT

The present invention is a needle assembly comprising a friction coating or material to prevent the needle assembly from prematurely disengaging from a needle holder. Preferably, the friction coating is UV curable acrylic or a spring washer.

12 Claims, 6 Drawing Sheets

ADHESIVE GASKET FOR BLOOD COLLECTION NEEDLES

BACKGROUND OF THE INVENTION

1. Field of the Invention

The present invention relates to a means for securely adjoining a blood collection needle and a needle holder. More particularly, this invention relates to a friction coating or material in cooperation with a needle assembly and a needle holder to prevent the needle assembly from prematurely disengaging from the needle holder.

2. Description of Related Art

Blood collection needle assemblies are typically used in conjunction with conventional needle holders in order to facilitate the collection of blood into a tube or several tubes. However, there is no means for preventing the needle from prematurely disengaging from the needle holder.

Therefore, a need exists to provide a means for preventing premature disengagement of a needle from a needle holder.

SUMMARY OF THE INVENTION

The present invention is a friction coating or material located on the hub of a needle. More particularly, the friction coating or material is located on the flange of the hub adjacent the threaded connection used to engage the needle assembly with a needle holder.

Preferably, the needle assembly of the present invention comprises a cannula and a hub. Preferably, the cannula is a conventional double ended needle. The hub comprises a threaded end, a ribbed end and a flange separating the threaded and ribbed ends. The flange comprises a threaded end surface and a ribbed end surface. The needle is connected to the hub whereby the needle comprises a non-patient end and an intravenous end.

Most preferably, the friction coating or material is located on the threaded end surface of the flange of the hub adjacent the threaded end. The friction coating or material may be located on only a portion or portions of the flange surface or on the entire flange surface.

Preferably, the friction coating is a solid elastomeric material, or another material with similar properties. Preferably, the friction coating is a thermoset adhesive and most preferably a UV curable acrylic thermoset adhesive such as for example, acrylated urethane. Preferably the thermoset adhesive cures rapidly to form flexible, transparent bonds when exposed to ultraviolet and/or visible light of sufficient irradiance. Preferably, the friction coating is a good adhesion coating between thermoplastics such as those used in medical devices.

A commercially available adhesive that may be used in the present invention is Loctite Product 3341 distributed by the Loctite Corporation of Rocky Hill, Conn.

Alternatively, the friction material may be a spring washer structure located on the entire surface area of the flange. The friction material may be metal or plastic.

A notable advantage of the present invention is that the friction coating or material is that it prevents a blood collection needle from "spinning-out" of its associated holder.

The "spinning-out" effect may be caused when a safety device is associated with the collection needle and the safety device is rotated or when an evacuated tube is inserted into the needle holder.

Another notable feature of the friction coating or material of the present invention is that it does not interfere with the normal and conventional methods of using blood collection devices.

DETAILED DESCRIPTION

Figure 1:
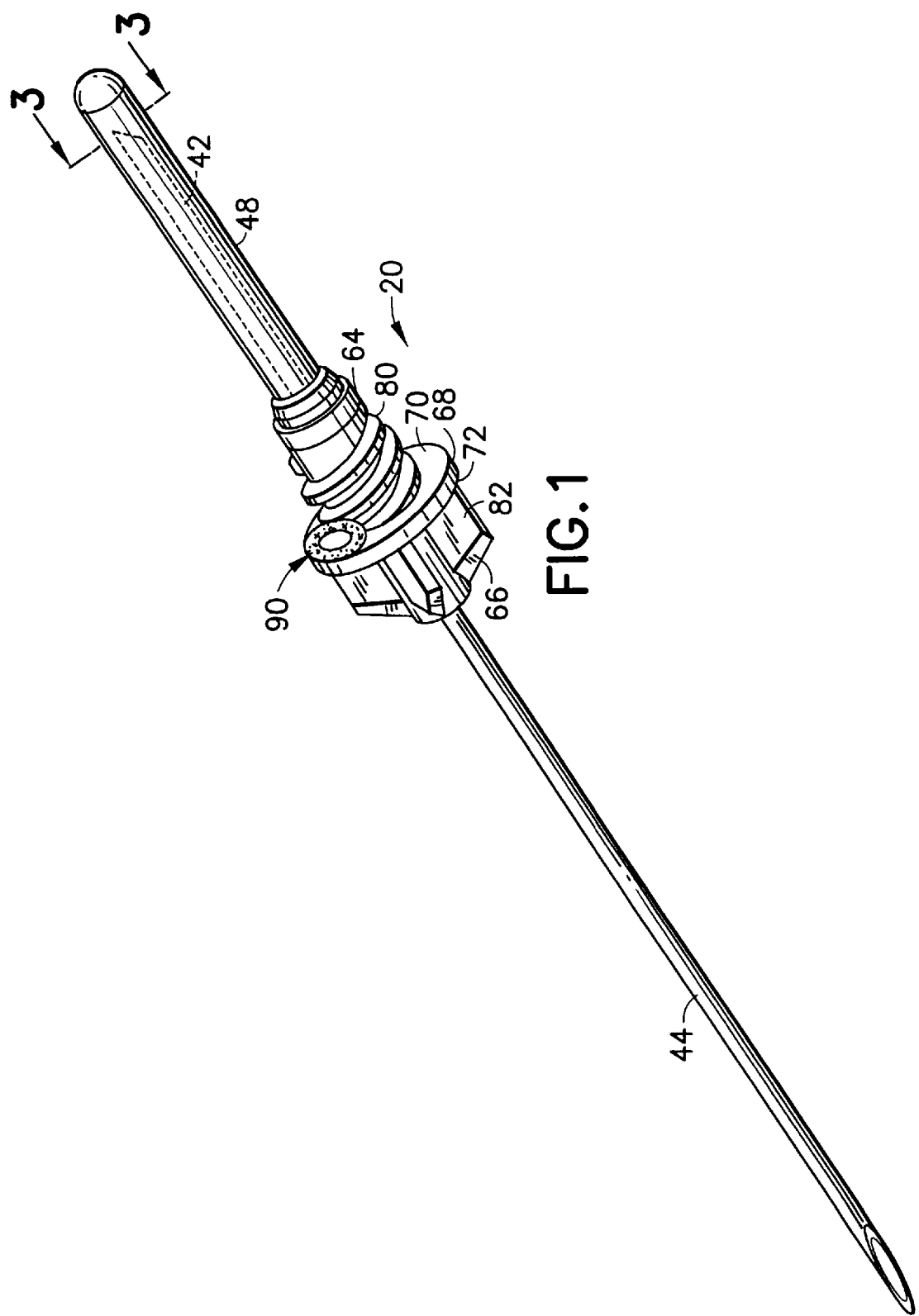
FIG. 1 is a perspective view of a needle assembly with a friction coating material on a portion of the flange surface.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 through 4 illustrate a needle assembly with the friction coating of the present invention. Needle assembly 20 includes a needle, a hub, and a friction coating.

Figure 2:
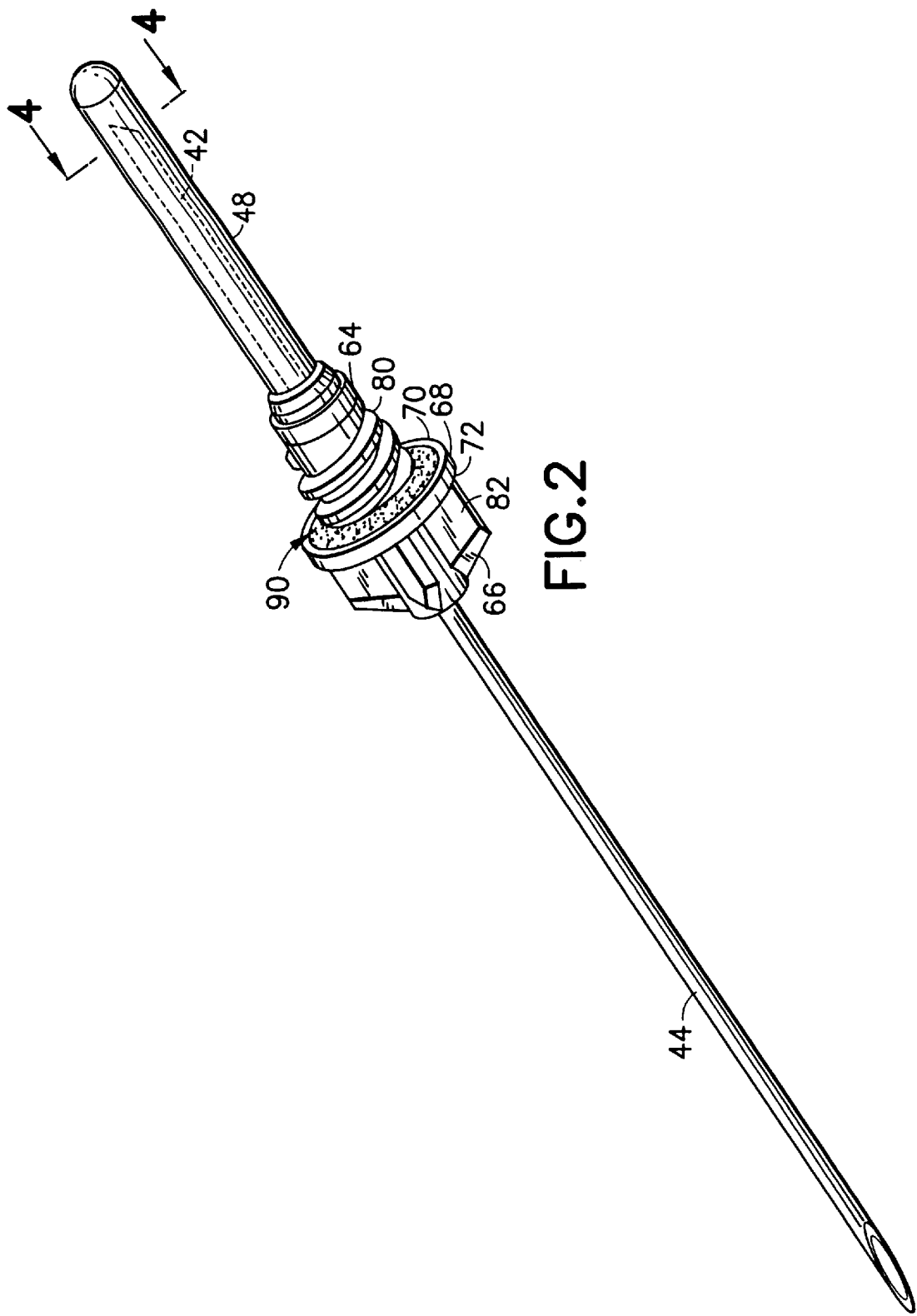
FIG. 2 is a perspective view of a needle assembly with a friction coating on a substantial portion of the surface of the flange.

As shown in FIGS. 1 and 2, the needle includes a non-patient end 42, an intravenous end 44 and a passageway extending between the non-patient end and the intravenous end. An elastomeric sleeve 48 covers the non-patient end.

As shown in FIGS. 1 and 2, hub includes a threaded end 64, a ribbed end 66 and a passageway extending between the threaded end and the ribbed end. Threaded end 64 and ribbed end 66 are separated by flange 68. Flange 68 includes a threaded end surface 70 a ribbed end surface 72. Non-patient end 42 of the needle extends from threaded end 64 and intravenous end 44 of the needle extends from ribbed end 66. Preferably, threaded end 64 comprises male threads 80 for mounting the hub on a conventional needle holder and ribbed end 66 comprises male ribs 82. As more particularly shown in FIGS. 3 and 4, friction coating 90 is located on threaded end surface 70 of flange 68.

Figure 3:
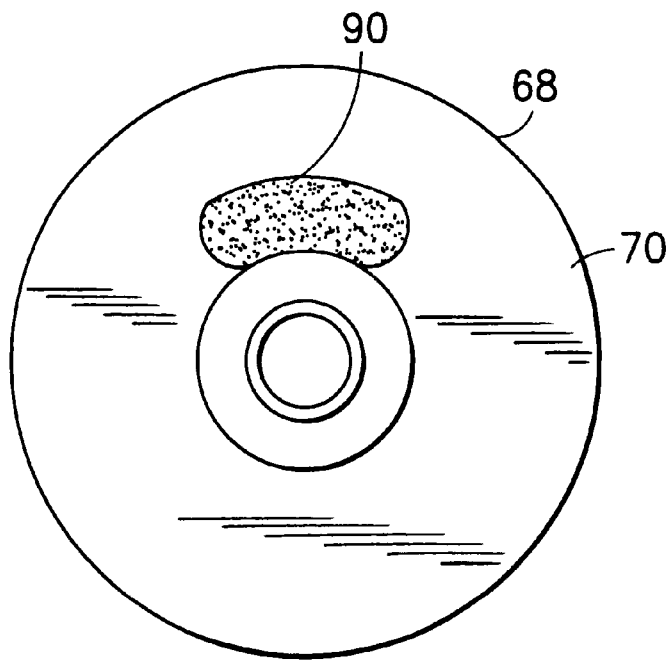
FIG. 3 is a top plan view of the needle assembly of FIG. 1 taken along line 3—3 thereof.
Figure 4:
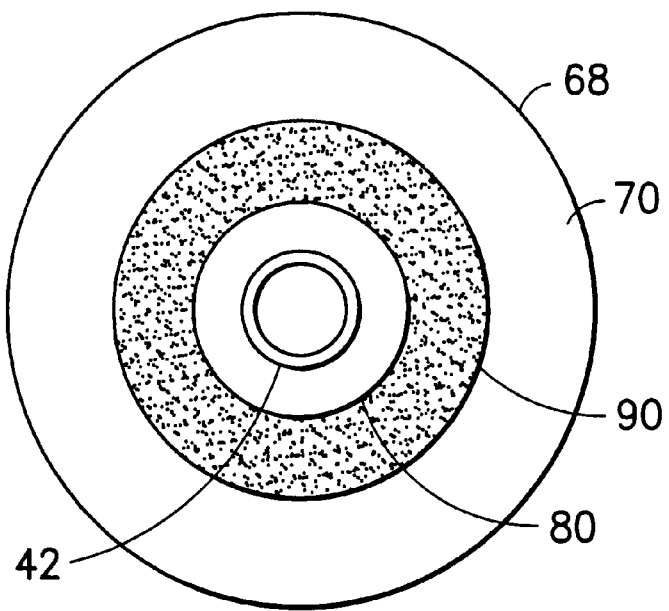
FIG. 4 is a top plan view of the needle assembly of FIG. 2 taken along line 4—4 thereof.

The needle assembly is assembled together whereby the needle is connected to the hub and sealed with adhesive at the ends of the hub. Friction coating 90 is added to the threaded end surface 70 of flange 68. It is within the purview of the invention that the friction coating or friction material may cover a portion, portions or the entire threaded end surface of the flange as shown in FIGS. 3 and 4.

Figure 5:
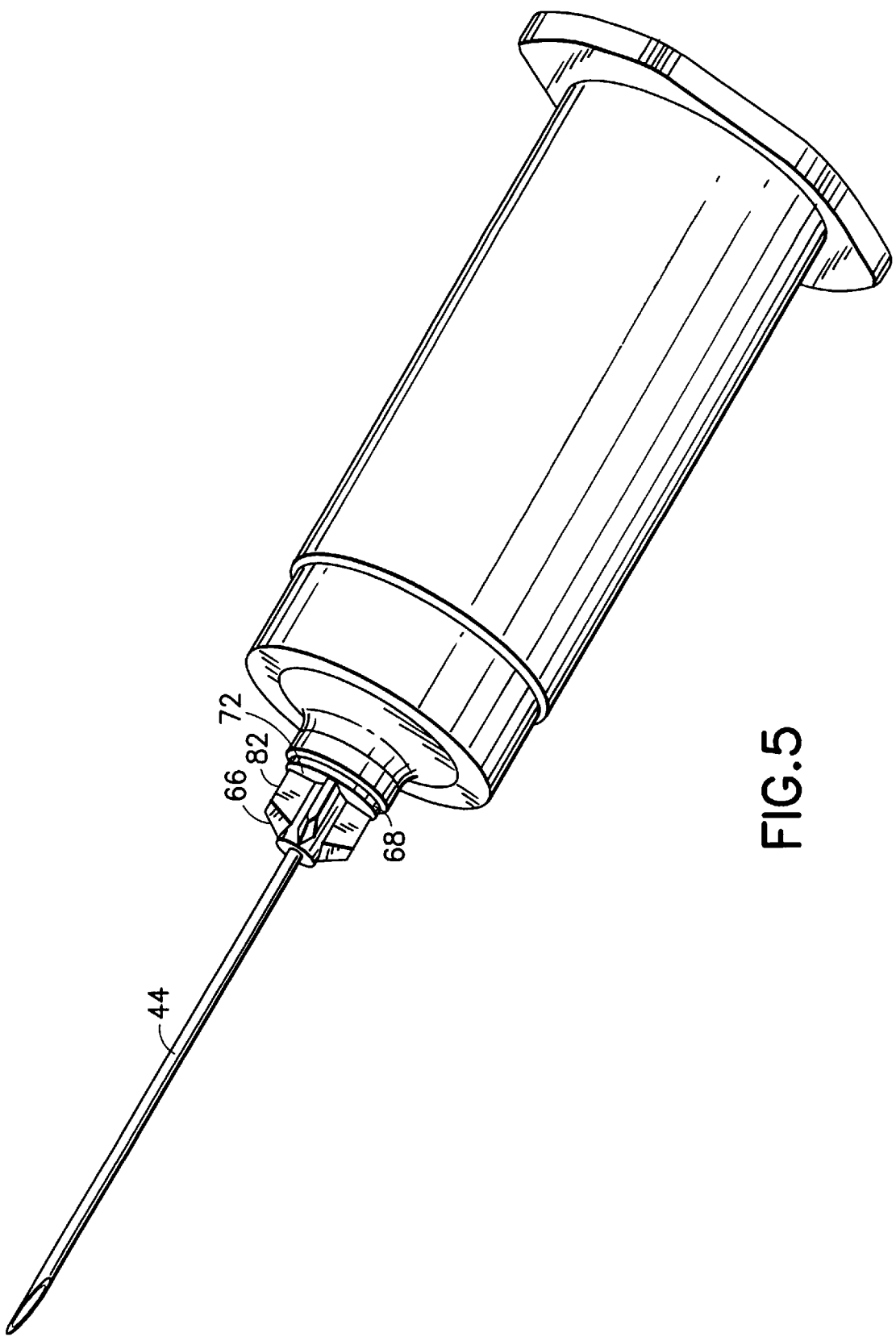
FIG. 5 is a perspective view of the needle assembly of FIG. 1 with a needle holder.

In use, a needle holder is screwed onto the hub of the needle assembly, as shown in FIG. 5, whereby the friction coating forms a removably secure adhesion between the threaded hub of the needle assembly and the needle holder during use. The friction coating allows the needle assembly to be removed from the needle holder in conjunction with a convention disposal container.

Figure 6:
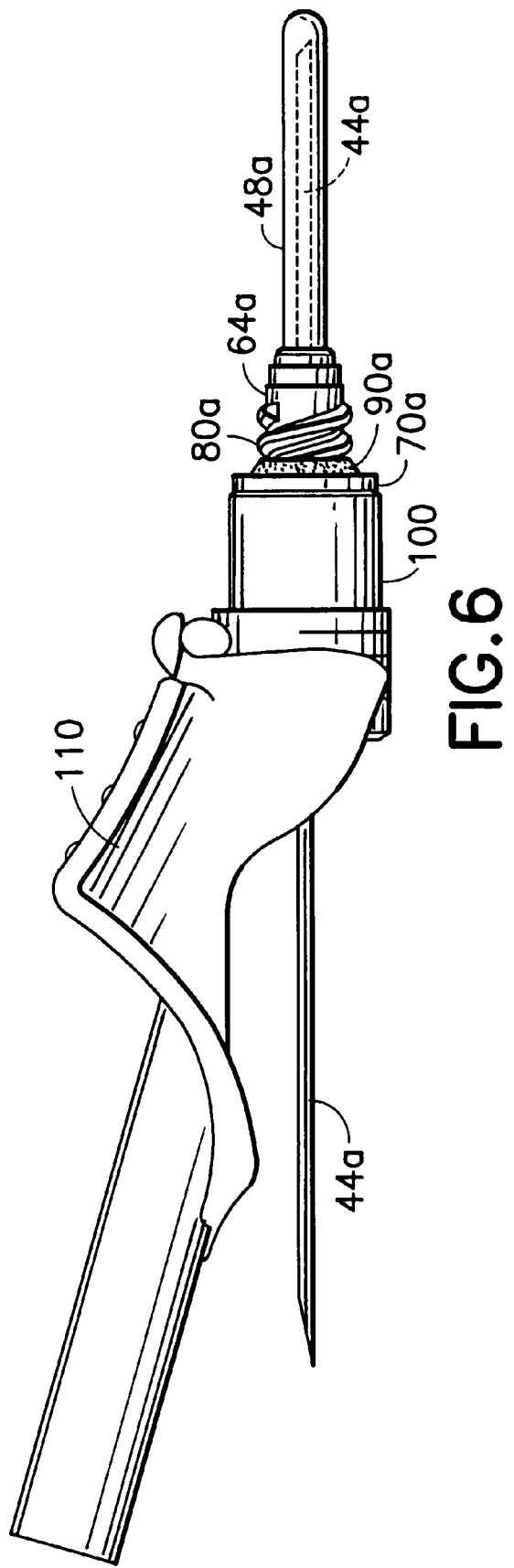
FIG. 6 is a perspective view of an alternative embodiment of a needle assembly with a safety device and a friction coating on the surface of the flange.

FIG. 6 is a further embodiment of the invention that includes many components which are substantially identical to the components of FIGS. 1–4. Accordingly, similar components performing similar functions will be numbered identically to those components of FIGS. 1–4, except that a suffix "a" will be used to identify those similar components in FIG. 6.

Alternatively, the needle assembly of the present invention may be used in conjunction with a safety shield assembly, as illustrated in FIG. 6.

A safety shield assembly comprising a shield 100 and a collar 110 are connected to needle assembly 20a. As shown in FIG. 6, friction coating 90a is located on threaded end surface 70a of flange 68a. In use, the needle holder is screwed onto the hub of the needle whereby the friction coating forms a removably secure adhesion between the needle assembly and the needle holder.

Figure 7:
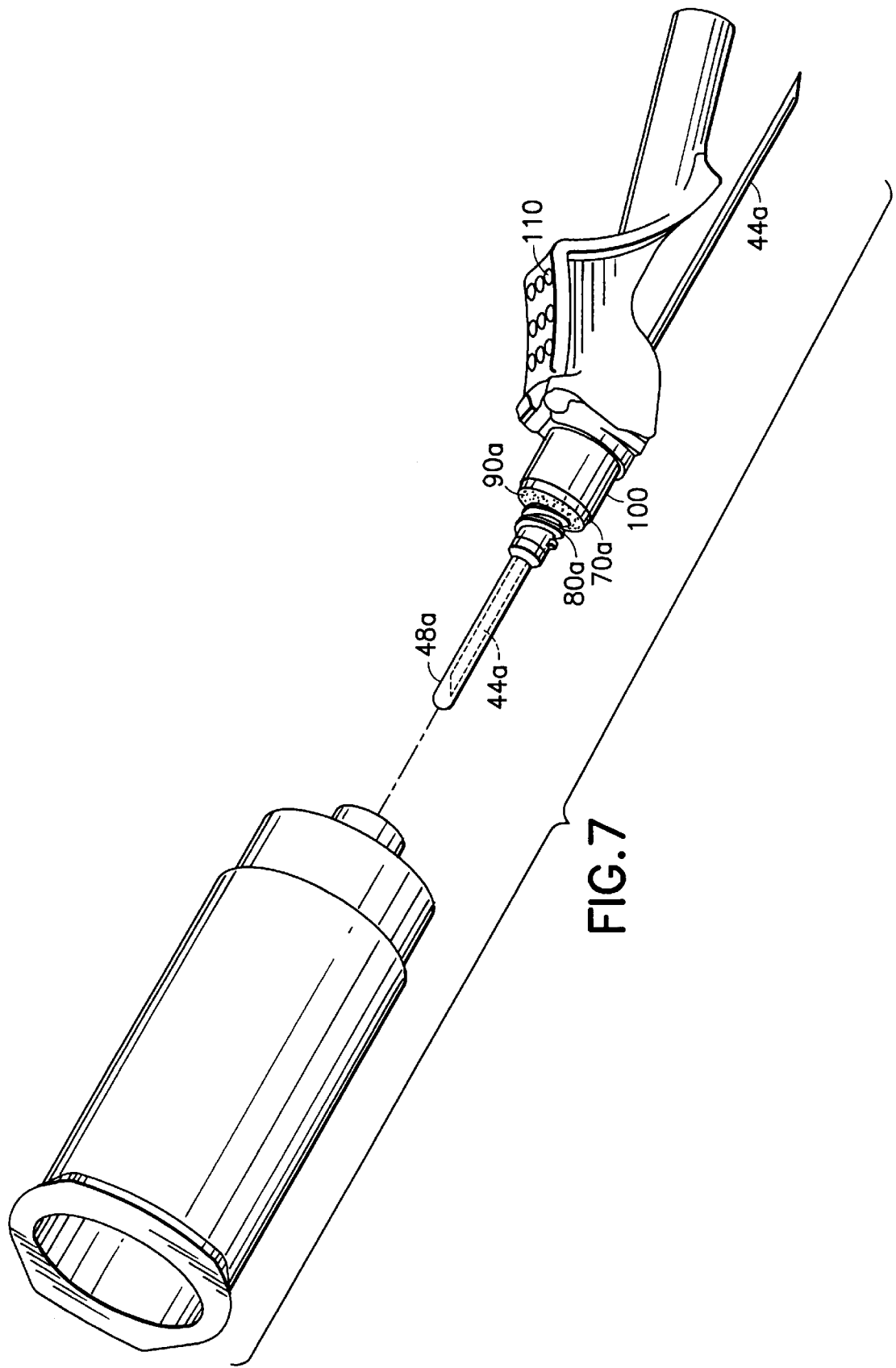
FIG. 7 is a perspective view of the needle assembly of FIG. 6 with a needle holder.

In use, as exemplified in FIG. 7, a needle holder is screwed onto the hub of the needle assembly with the safety shield whereby the friction coating forms a removably secure adhesion between the threaded hub of the needle assembly and the needle holder during use. The friction coating allows the needle assembly to be removed from the needle holder in conjunction with a convention disposal container.

What is claimed:

1. An assembly comprising:
   a hub comprising a threaded end, a ribbed end, a flange separating said threaded end and said ribbed end comprising a threaded end surface and a ribbed end surface;
   a needle connected to said hub comprising a non-patient end and an intravenous end; and
   a friction coating located on said threaded end surface of said flange, whereby said friction coating forms a removably secure adhesion between said threaded hub of said needle assembly and a needle holder.

2. The assembly of claim 1, wherein said friction coating is a solid elastomeric material.

3. The assembly of claim 2 wherein said solid elastomeric material is a thermoset adhesive.

4. The assembly of claim 3, wherein said thermoset adhesive is a UV curable acrylic thermoset adhesive.

5. The assembly of claim 3, wherein said thermoset adhesive is acrylated urethane.

6. The assembly of claim 1, wherein said friction coating is a spring washer.

7. An assembly comprising:
   a hub comprising a threaded end, a ribbed end, a flange separating said threaded end and said ribbed end comprising a threaded end surface and a ribbed end surface;
   a needle connected to said hub comprising a non-patient end and an intravenous end;
   a collar connected to said hub; and a shield movably connected to said collar;
   a needle holder; and
   a friction coating located on said threaded end surface of said flange, whereby said friction coating forms a removably secure adhesion between said threaded hub of said needle assembly and a needle holder.

8. The assembly of claim 7, wherein said friction coating is a solid elastomeric material.

9. The assembly of claim 8, wherein said solid elastomeric material is a thermoset adhesive.

10. The assembly of claim 9, wherein said thermoset adhesive is a UV curable acrylic thermoset adhesive.

11. The assembly of claim 9, wherein said thermoset adhesive is acrylated urethane.

12. The assembly of claim 7, wherein said friction coating is a spring washer.

* * * * *